United States Patent
Damadian et al.

(10) Patent No.: US 11,103,149 B1
(45) Date of Patent: Aug. 31, 2021

(54) METHOD AND SYSTEM FOR PERFORMING UPRIGHT MAGNETIC RESONANCE IMAGING OF VARIOUS ANATOMICAL AND PHYSIOLOGICAL CONDITIONS

(71) Applicant: Fonar Corporation, Melville, NY (US)

(72) Inventors: Raymond V. Damadian, Woodbury, NY (US); Ki-Cheung Chu, Kings Park, NY (US)

(73) Assignee: Fonar Corporation, Melville, NY (US)

( * ) Notice: Subject to any disclaimer, the term of this patent is extended or adjusted under 35 U.S.C. 154(b) by 703 days.

(21) Appl. No.: 15/720,747

(22) Filed: Sep. 29, 2017

Related U.S. Application Data

(60) Continuation of application No. 14/291,265, filed on May 30, 2014, now abandoned, which is a continuation of application No. 13/679,405, filed on Nov. 16, 2012, now abandoned, which is a division of application No. 12/832,623, filed on Jul. 8, 2010, now abandoned.

(60) Provisional application No. 61/270,405, filed on Jul. 8, 2009.

(51) Int. Cl.
*A61B 5/055* (2006.01)
*A61B 5/026* (2006.01)
*A61B 5/00* (2006.01)

(52) U.S. Cl.
CPC .......... *A61B 5/0263* (2013.01); *A61B 5/0044* (2013.01)

(58) Field of Classification Search
CPC ...... G06F 2111/10; G06F 30/23; G06T 17/20; G06T 2207/10081; G06T 2207/10088; G06T 2207/20068; G06T 2207/30061; G06T 2210/24; G06T 2210/41; G06T 7/0012; G16H 50/50
See application file for complete search history.

(56) References Cited

U.S. PATENT DOCUMENTS

| | | |
|---|---|---|
| 4,175,128 A | 11/1979 | Taylor |
| 6,182,029 B1 | 1/2001 | Friedman |
| 6,225,805 B1 | 5/2001 | Damadian et al. |
| 6,414,490 B1 | 7/2002 | Damadian et al. |
| 6,514,226 B1 | 2/2003 | Levin et al. |
| 6,677,753 B1 | 1/2004 | Danby et al. |
| 2001/0037063 A1 | 11/2001 | Albert et al. |
| 2003/0064024 A1 | 4/2003 | Driehuys et al. |

(Continued)

OTHER PUBLICATIONS http://medical-dictionary.thefreedictionary.com/p/pulmonary%20congestion obtained from the Internet on Nov. 25, 2014.

(Continued)

*Primary Examiner* — Mark D Remaly
(74) *Attorney, Agent, or Firm* — Lerner, David, Littenberg, Krumholz & Mentlik, LLP

(57) ABSTRACT

Vasculature or parenchyma is imaged using upright MRI techniques, on patients who may have conditions such as congestive heart failure, or otherwise be healthy. When an individual is horizontal, venous drainage is minimized, causing the vessels to remain engorged, also referred to herein as vascular congestion. Vascular congestion results in an enlarging of the vessels and surrounding tissue causing the vessels to be more visible on MRIs. The decrease in vascular visibility in upright subjects is in part, due to an increase in venous drainage. Patients suffering from coronary and/or pulmonary deficiencies (e.g. CHF) experience decreased rates and degrees of venous drainage. In one embodiment, the present invention uses upright imaging to visualize these enlarged vessels.

3 Claims, 12 Drawing Sheets

(56) References Cited

U.S. PATENT DOCUMENTS

| | | |
|---|---|---|
| 2003/0130574 A1 | 7/2003 | Stoyle |
| 2004/0204644 A1 | 10/2004 | Tsougarakis et al. |
| 2006/0264764 A1 | 11/2006 | Ortiz-Burgos |
| 2007/0264200 A1 | 11/2007 | Small et al. |
| 2009/0048505 A1 | 2/2009 | Kuth et al. |
| 2011/0093243 A1 | 4/2011 | Tawhai et al. |

OTHER PUBLICATIONS

Haaga et al, CT and MR Imaging of the Whole Body, Volume One and Two Fourth Edition, 2003, Mosby Inc. pp. 17,49,50,93,208,214,341,366,838.

Upright    Supine    Prone

Upright  Supine  Prone

Upright　　　　　　Supine　　　　　　Prone

Upright  Supine  Prone

Upright　　　　Supine　　　　Prone

Upright　　　　Supine　　　　Prone

METHOD AND SYSTEM FOR PERFORMING UPRIGHT MAGNETIC RESONANCE IMAGING OF VARIOUS ANATOMICAL AND PHYSIOLOGICAL CONDITIONS

CROSS-REFERENCE TO RELATED APPLICATIONS

The present application is a Continuation of U.S. patent application Ser. No. 14/291,265, filed May 30, 2014, which is a Continuation of U.S. patent application Ser. No. 13/679,405, filed Nov. 16, 2012, which is a Divisional of U.S. patent application Ser. No. 12/832,623, filed Jul. 8, 2010, which claims the benefit of U.S. Provisional Patent Application No. 61/270,405 filed Jul. 8, 2009, all of which are hereby incorporated herein by reference.

BACKGROUND

Magnetic resonance imaging ("MRI") offers numerous advantages over other imaging techniques. MRI does not expose either the patient or medical personnel to X-rays and offers important safety advantages. Also, MRI can obtain images of soft tissues within the body which are not readily visualized using other imaging techniques. This feature makes MRI particularly useful in analyzing the parenchymal lung tissue and pulmonary vasculature in certain patients.

Different tissues produce different signal characteristics. Tissues having a high density of nuclei will produce stronger signals than tissues with a low density of such nuclei. Furthermore, relatively small gradients in the magnetic field are superimposed on the static magnetic field at various times during the process, so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

Conventionally, MRI machines require that a patient lie in a horizontal position and then be advanced into a tubular enclosure within a super-conducting solenoidal magnet used to generate the static magnetic field. This method of imaging creates a unique challenge with some patients. For example, patients with congestive heart failure, or other cardiac or pulmonary related conditions, may experience orthopnea (the respiratory resistance of the lungs increases upon transitioning from the seated to the supine posture). when placed in relatively supine or horizontal positions. This makes obtaining accurate diagnostic images of these patients very difficult. Ferromagnetic frame magnets having horizontal pole axes have been developed, which alleviate the some of these difficulties.

Ferromagnetic frame magnets having horizontal pole axes have been disclosed, for example, in commonly assigned U.S. Pat. No. 6,414,490, the disclosures of which are incorporated by reference herein, and U.S. Pat. No. 6,677,753, filed on Nov. 22, 2000, the disclosure of which is also incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a supine or recumbent position, the bed can be tilted and/or elevated so as to image the patient in essentially any position between a fully standing position and a fully supine or fully recumbent position, and can be elevated or lowered so that essentially any portion of the patient's anatomy is disposed within the gap in an optimum position for imaging. As further disclosed in the aforesaid patents, the patient positioning device may include additional elements such as a platform, any type of seat, or both, projecting from the bed to support the patient when the bed is tilted towards a standing orientation. Still, other patient supporting devices can be used in place of a bed in a system of this type. Thus, magnets of this type provide extraordinary versatility in imaging.

FIG. 12 of the current application shows a sectional view of an MRI magnet subsystem 100. MRI magnet subsystem 100 includes a magnet having a ferromagnetic frame 102, a flux generating means 104 as is described in further detail below, and a patient handling system 106. The ferromagnetic frame 102 includes a first side wall 108 and a second side wall 110. The side walls 108 and 110 extend vertically. For purposes of clarity, FIG. 12 does not show the second side wall 110 or any of its associated structures (see FIG. 5). The ferromagnetic frame 102 also includes a top flux return structure 112 and a bottom flux return structure 114. The top flux return structure 112 may include two columns 116 and 118. Between these two columns, a top opening 120 is defined. Similarly, the bottom flux return structure 114 may include two columns 122 and 124 that together define a bottom opening 126. Thus, the side walls 108 and 110 and the flux return members 112 and 114 form a rectilinear structure, with the top flux return structure 112 constituting the top wall of the rectilinear structure, the bottom flux return structure 114 constituting the bottom wall of the rectilinear structure and the side walls 108 and 110 forming the side walls of the rectilinear structure. The frame 102 of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole 134. The first magnetic pole 132 extends from the first side wall 108 towards the second side wall 110 and the second magnetic pole 134 extends from the second side wall 110 towards the first side wall 108. Magnetic poles 132 and 134 are generally cylindrical and are coaxial with one another on a common horizontal polar axis 136. Between the magnetic poles 132 and 134 is a gap 131, also referred to as the patient-receiving space, of the magnet. The gap or patient-receiving space 131 is accessed by the front patient opening 128, the back patient opening 130, the top opening 120 or the bottom opening 126.

The flux generating means 104 includes a first electromagnetic coil assembly 138 which surrounds the first magnetic pole 132, and a second electromagnet coil assembly 140, which surrounds the second magnetic pole 134. As previously noted, these electromagnetic coil assemblies 138 and 140 may be either resistive or superconductive.

The patient handling system 106 is capable of three degrees or axes of motion. The patient handling system 106 may be termed a stand-up patient handling system, although the patient handling system 106 is not limited to standing position applications. The patient handling system 106 includes a carriage 142 mounted on rails 144. The carriage 142 may move linearly back and forth along the rails 144. The rails 144 typically do not block the bottom open space 126.

A generally horizontal pivot axis 146 is mounted on carriage 142. An elevator frame 148 is mounted to the pivot axis 146. The carriage 142 is operable to rotate the elevator frame 148 about the pivot axis 146. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement or motion. Specifically, the patient handling system 106 can move a patient 154 in two linear directions and also rotate patient 154 around an axis. The solid black arrows of FIG. 12 show the three axes of movement possible with the patient handling system 106. Note that often the rails 108 are mounted such that portions of patient 154 may be positioned below the rails through bottom open space 126.

Often, a foot rest 156 may be used in order to support a patient in a standing position. Given the wide variety of positions possible with the patient handling system 108, many other such supports may be implemented, such as chair seats or straps.

The patient handling system 106 incorporates one or more actuators 103 and an actuation control unit 105. Actuators 103 may be conventional electrical, electromechanical, pneumatic, hydraulic or other devices capable of imparting the desired motion to the elements of the patient handling system. For example, the actuators may include elements such as conventional stepper motors or other conventional electric motors linked to the elements of the patient handling system 106. The actuator control unit 105 may incorporate a conventional programmable controller, microprocessor, or computer with appropriate input and output interfaces. As further discussed below, the actuation control unit 105 is linked to a control computer and to the manual controls which regulate the patient handling system. The actuation control unit may be mounted in proximity to the actuators 103 as, for example, on carriage 142.

Of utility then are methods and systems for obtaining accurate diagnostic images of a patient's anatomy, as for example, patients with cardiac or pulmonary related maladies. These images can then be used for diagnosis of disease.

BRIEF SUMMARY OF THE INVENTION

One aspect of the present invention provides a method for evaluating vasculature using magnetic resonance imaging comprising the steps of placing a patient into a magnetic resonance imaging apparatus with the patient in an upright position, capturing magnetic resonance images of the patient's vasculature, and evaluating the patient's vasculature based on one or more of the magnetic resonance signal characteristics of the captured images. This particular method can be used to image any type of vasculature, including but not limited to lung, kidney and or liver vasculature. This particular aspect of the present invention is also useful to diagnose the presence or absence of congestive heart failure.

The present invention is not limited only to the use of MR signal intensity to perform the methods described herein. In other another aspects of the present invention, any type of MR signal characteristic (e.g. signal phase, signal frequency and signal amplitude) can be used either independently, or in combination with one another, to aid the clinician in making clinical determinations about vasculature, parenchyma and or cardiac function.

Another aspect of the present invention provides a method for evaluating parenchyma from magnetic resonance images, comprising placing a patient into a magnetic resonance imaging apparatus with the patient in an upright position, capturing magnetic resonance images of the parenchyma of a selected organ or organs, and using one or more magnetic resonance signal characteristics to evaluate the imaged parenchyma. This particular aspect of the invention is also used to image lung, kidney and liver parenchyma. This aspect of the present invention is also used to diagnose the presence or absence congestive heart failure and also evaluate gravitational effects on the human lungs.

In a preferred embodiment of the present invention, a method for evaluating parenchyma vasculature from magnetic resonance images, comprising the steps of placing a patient into a magnetic resonance imaging apparatus with the patient in an upright position, capturing magnetic resonance images of the parenchyma of a selected organ or organs, and using one or more magnetic resonance signal characteristics to evaluate the imaged parenchyma. In yet another embodiment, this particular aspect of the present invention is used to diagnose the presence or absence of heart failure.

In yet another preferred embodiment of the present invention a magnetic resonance imaging magnet comprises a magnet frame having a pair of pole faces spaced apart from one another along a horizontal pole axis and defining a patient-receiving space therebetween, supports holding said frame so that said pole axis is above a floor of a structure so that a patient may enter said patient-receiving space by moving across said floor of said structure, a magnetic flux generator operable to provide magnetic flux in said patient-receiving space, and a rotatable patient support positioned in the patient receiving and rotatable between a horizontal position and an upright, and wherein said patient is supported in an upright position and magnetic resonance images of a patient are obtained in the upright position, the images displaying information useful in determining vasculature or parenchyma wherein said magnetic resonance imaging magnet is used for upright imaging of vasculature and parenchyma. In a further embodiment of this particular aspect of the present invention, lung vasculature and parenchyma are imaged. In yet another embodiment, those images are used to diagnose the presence or absence of congestive heart failure.

DETAILED DESCRIPTION

General

Figure 1:
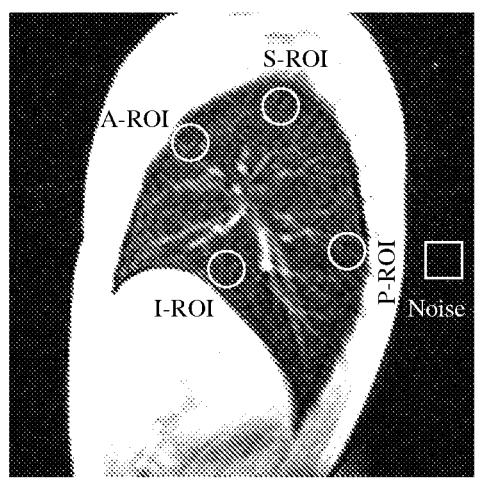
FIG. 1. depicts magnetic resonance ("MR") images of locations of the 4 regions of interest ("ROIs") in a mid-sagittal slice of the right lung used in quantitative analysis. The 4 white circles indicate where the anterior ROI (A-ROI), posterior ROI (P-ROI), superior ROI (S-ROI), and inferior ROI (I-ROI) were drawn to calculate the signal intensity of lung parenchyma. The white square outside the body depicts the region used to estimate noise.

As described in greater detail in commonly assigned U.S. Pat. Nos. 6,414,490 and 6,677,753, the disclosures of which are hereby incorporated by reference, an MRI system, including one capable of upright imaging, can be provided with a patient support, such as a bed or table or any equivalent thereof, which can extend in a generally vertical direction so that the long axis of the patient is generally vertical. For example, the patient may be in an essentially standing posture, with his back, side or front leaning against a generally vertical patient support. In other arrangements, the support includes a seat projecting from the table so that the seat is in a horizontal plane when the table surface is substantially vertical. In particularly preferred arrangements, the patient support can move relative to the magnet and may be arranged to tilt through a range of orientations between a generally horizontal orientation and a generally vertical orientation.

Not many imaging modalities can handle upright imaging, largely because of the construction of the scanner itself. Chest radiography, scintigraphy, and MRI are among the few modalities that can image human lungs in an upright position. Besides specific differences in the type and quality of information offered by these modalities, chest x-ray and scintigraphy expose the patient to radiation, while MRI has the advantage of being radiation free. This radiation free imaging modality is beneficial for upright imaging in general, and for lung imaging in particular.

In preferred embodiments, "Upright" as used herein generally refers to any patient position between about 0.1° and about 90°, relative to a horizontal table, and may include positions where the patient's upper body is at an angle greater than 90° with respect to a horizontal position. This angle would be seen if the patient was required to lean forward. In yet other embodiments, "Upright" may refer to a patient positioned between a recumbent and seated position. "Upright" may also refer to the patient can be standing or in a standing position, seated or in a seated position. UPRIGHT® is also a registered trademark of the Fonar Corporation. "Upright" as used herein is not intended to refer to the goods identified by the registered trademark, unless indicated with a "®".

Lung anatomy and functionality are very sensitive to body postures in both healthy people and sick patients. The nature of illnesses affecting pulmonary and/or cardiac function affect a person's ability to lay down and maintain an adequate level of respiration, without experiencing discomfort and orthopnea. Clinically, this has been particularly evident in some common life-threatening diseases such as congestive heart failure (CHF) and acute respiratory distress syndrome (ARDS), but can be seen in any illness or condition affecting the pulmonary or circulatory systems. For example, many CHF patients have to sit up to be able to breathe during orthopnea.

CHF patients also may experience coughing which, can at times be both extensive and debilitating. This presents a challenge for the clinician performing the imaging, as the patient's movement may prevent an accurate image from being taken. In the recumbent position, the patient may not be able to hold still long enough for the image to be taken, due to orthopnea or discomfort. In the upright position, patient comfort is maximized, while coughing episodes and accessory breathing is minimized. This makes upright imaging desirable for such patients, as they may not be able to withstand recumbent imaging.

In accordance with an aspect of the present invention, when an individual transitions from an essentially supine or prone position, to an essentially upright position, images of the pulmonary vasculature can be captured at different points along the range of positions. In this regard, the present invention is not limited to imaging in any one position. In preferred embodiments, the patient is positioned at a point of comfort with the patient's upper body forming a longitudinal plane, with the plane being positioned at an angle generally between 0.1° and 90° relative to a horizontal table.

Upright posture also offers an extra degree of freedom to study and maximize gravitational effects on the lungs and pulmonary vasculature, compared to mere supine versus prone studies. Furthermore, imaging in the upright posture is more relevant to the human condition as we spend the majority of our lives walking, standing and sitting. This work on any subject, whether sick or healthy, and irregardless of the severity of the illness, will help clinicians to evaluate gravitational effects on the human lungs.

The posture dependency of pulmonary functions in CHF patients also highlights the extremely close and inseparable relationship between the heart and the lungs, and their respective physiological systems. MRI of the lungs can serve as a surrogate marker of cardiac functions without going through an often-invasive cardiac work-up. Coupled with upright capability, the multi-posture MR lung imaging described herein may offer a new means of evaluating the extent of cardiac failure and its concomitant systemic effect on systems such as the pulmonary system. It may also aid in understanding how systemic physiological systems effect cardiac failure.

Because of the benefits of the present invention, patients who typically would experience orthopnea when subjected to traditional supine MR imaging, can now be imaged in more upright positions. One aspect of the present invention allows for better imaging of these types of patients because the upright positioning prevents orthopnea in many types of patients. The diminished degree of orthopnea subsequently leads to a decrease in excessive movement, ultimately leading to a more clinically accurate scan (e.g. a scan substantially void of artifact).

Parenchyma and MR Signal

Upright MR imaging of organ tissue can be used to evaluate the presence of fluid and parenchyma, based on the MR signal strength. In particular, the parenchymal lung tissue can be imaged using MR for this purpose. This contributes to the present invention in that it demonstrates the ability of diagnosing and evaluating conditions such as CHF, without having to expose a patient to radiation or a posture that will induce severe respiratory distress.

A main contributor to lung parenchyma MR signal is the blood volume in the lungs. It is well known that venous drainage from the lungs is enhanced in the upright posture compared to the recumbent posture. This reduction of blood volume in the lungs could explain the drop of lung parenchyma MR signal intensity and vessel conspicuity in the upright posture compared to the recumbent postures. Other contributing factors include blood perfusion, diffusion of lung water, and lung density. For example, the lungs are more distended in the superior/inferior (S/I) direction when upright, hence reducing lung density and further decreasing the lung parenchyma MR signal intensity which is a per unit volume parameter.

MR signal intensity is likely to be lower, and in some cases, significantly lower, in the upright position than in the recumbent postures. It is also expected that there should not be a significant difference between MR intensity in the prone and supine positions. As expected, the overall signal to noise ratio ("SNR") will also be lower in the upright posture. Blood vessel conspicuity should also be lower in the upright position compared to the recumbent positions. While not intending to be bound to a particular theory, the decreased MR intensity and decreased vessel conspicuity in the upright images is largely due to decreased blood volume in the lungs, in part due to increased venous drainage in the upright position. Blood perfusion, diffusion of lung water and lung density may also contribute to these results. Since the lungs have greater volume when the subject is upright, the lung tissue is less dense. The decreased density of the parenchymal tissue will generate a weaker MR signal.

While imaging of lung parenchyma is described in detail herein, the present invention is by no means limited to imaging lung parenchyma. The upright MR imaging techniques described can be used to directly image the parenchyma of any organ, including but not limited to the liver, kidneys, spleen, gall bladder and intestines.

Imaging Vasculature

In one embodiment of the present invention, vasculature can be imaged using upright MRI techniques on patients who are healthy, or who may have conditions such as CHF. Vasculature is defined herein according to its plain and ordinary meaning, and can include all types of blood vessels including veins, venules, arteries, arterioles, capillaries, and their surrounding vascular beds.

When an individual is essentially horizontal, venous drainage is minimized, causing the vessels to remain engorged, and simultaneously enlarged, also referred to herein as vascular congestion. Vascular congestion results in an enlarging of the vessels and surrounding tissue, causing the vessels to be more visible on MRIs.

In CHF patients, decreased rates and degrees of venous drainage result in vascular congestion. Vascular congestion is prevalent and presents not only when the patient is recumbent, but when upright as well. These enlarged vessels and their surrounding tissues (e.g. parenchyma), can be visualized using upright MRI techniques, and may be useful to evaluate and diagnose heart failure.

Heart failure (CHF) can be classified into different categories, based on which side of the heart is affected. Right-sided heart failure affects the right ventricle, while left-sided failure affects the left ventricle. Typically, left-sided heart failure affects the lungs and pulmonary system and results in pulmonary edema, while right-sided heart failure generally affects systemic organs, for example but not limited to the kidneys and liver.

In aspects of the present invention, upright MR imaging of the vasculature of organs and their surrounding tissues can be performed. In preferred embodiments of the present invention, upright MR imaging is used to image the lungs. Patients who have enlarged or congested vasculature as a result of CHF are ideal candidates for the MRI techniques described herein because of the likelihood of the presentation of vascular congestion. Any patient having vasculature congestion, regardless of the etiology, can be imaged using the techniques described herein.

Another aspect of the present invention includes a method for evaluating pulmonary vasculature from magnetic resonance images, comprising the steps of: placing a patient into a magnetic resonance imaging apparatus with the patient in an upright position; capturing magnetic resonance images of the patient's lungs; using said magnetic resonance signal intensity to evaluate the pulmonary vasculature; and evaluating the patient's cardiac function based on presence of the fluid.

Cardiac Function

Another aspect of the present invention includes a method for evaluating cardiac function based on the presence of lung fluid as determined from magnetic resonance images, comprising the steps of placing a patient into a magnetic resonance imaging apparatus with the patient in an upright position; capturing magnetic resonance images of the patient's lungs; measuring magnetic resonance signal intensity from the images of the patient's lung parenchyma; using the magnetic resonance signal intensity to identify the presence of fluid in the lungs; and evaluating the patient's cardiac function based on presence of the fluid.

As MR imaging is sensitive to the presence of fluid in tissue, an increase in fluid (e.g., pulmonary edema) will result in an increased MR intensity in the lung parenchyma. As pulmonary edema is a common symptom of congestive heart failure, the MR values will help the clinician to determine how much fluid is present in the lungs. Once the clinician makes this determination, they then correlate the presence of pulmonary edema (from the MR image) with cardiac output.

Physiological changes occur in the lungs when the patient is moved from a recumbent to an upright position. These changes are largely evident in MR images due to variations in the presence of fluid. This is particularly evident when fluid distribution is observed in the lung parenchyma and/or vasculature. In addition to signal intensity, blood vessel visibility and MR signal intensity gradation can also be used to evaluate lung vasculature and cardiac function.

In another aspect of the present invention, a difference, or lack there of between the signal characteristics in upright and recumbent readings, could indicate a presence or absence of disease, or compromised cardiac function. While not intending to be bound to a particular theory, this difference in signal characteristic may be due, in part to the fact that CHF patients will exhibit higher signal intensity in the upright position, when compared to healthy patients.

Adding breath-holds such as FRC (Functional residual capacity, i.e. normal tidal expiration) and TLC (Total Lung Capacity) may add to the imaging capabilities of certain embodiments of the present invention.

In addition to the presence of fluid in the lungs, the presence of fluid in other organs such as the kidneys and liver may also indicate the onset of congestive heart failure.

Furthermore, the extent of the MR signal strength generated could indicate the extent of disease present. A stronger signal would result from more fluid being present in the organ(s), therefore indicating a more advanced stage of heart failure. Clinician's will ultimately choose which organs and/or vasculature get imaged based on sound clinical diagnosis. The organs believed to be involved in a particular disease would be the organs the clinician selects.

Additionally, comparing the MR signals of different organs may help the clinician determine whether a patient is suffering from left-sided heart failure, right-sided heart failure, or bi-ventricular failure. For example, an upright MR image exhibiting a strong signal from the parenchyma of the lungs may indicate left-sided heart failure, while a strong MR signal from the parenchyma of the kidneys may indicate right-sided heart failure. A strong MR signal from both the lung and kidney parenchyma may indicate bi-ventricular heart failure. Changes in the MR signal in the parenchyma of a given organ may indicate the progression of disease, while weak MR signal, particularly in the upright position may indicate the absence of disease. Furthermore, MR images of parenchyma and vasculature can be used to detect various diseases, such as heart failure and kidney failure.

Cardiac and pulmonary function imaging are generally conducted as separate disciplines. Being able to correlate findings between the two domains in the same imaging session and posture is of tremendous value.

EXAMPLES

The following example describes a study performed using upright lung MR imaging on four volunteer subjects.

Scans were performed on the UPRIGHT® MRI scanner (Fonar Corporation, New York) at 0.6 T. With a vertical walk-in patient space, the scanner has a bed that can be rotated to any angle between the vertical and horizontal position. As a result, the patient can be scanned standing up, sitting up, flexing, extending, and lying horizontally or in the reverse-Trendelenburg position. When combined with various patient orientations such as feet first head last, Trendelenburg and lateral decubitus positions are also possible.

Four non-smoking healthy human volunteers participated in this study (2 males/2 females, age: 22-54). A body RF transmitter coil was used for RF excitation. A separate rigid thoracic coil (quadrature receive-only) with a homogenous illumination was centered on the lungs. The imaging parameters were selected according to clinical parameters commonly known in the art. Those imaging parameters included the following: the MR pulse sequence used was a 2D multi-slice gradient echo FLASH sequence with a very short time to echo ("TE"): TR=80 ms, TE=0.9 ms, flip angle=25°, receive bandwidth=625 Hz/pixel, slice thickness/gap=16 mm/2 mm, field-of-view=40 cm, number of excitation=1, matrix=128×128 zipped to 256×256. Scan time was about 10 s, covering the entire lungs with multiple slices within a single breathhold. Each volunteer was scanned in 3 postures (seated upright, recumbent supine and prone, in variable order) and in the 3 orthogonal planes (axial, coronal, and sagittal) at end expiration (residual volume ("RV")) to maximize lung parenchyma MR signal. They were given about 10 minutes to settle down in each posture prior to the above scans. All images were windowed identically for direct comparison. While the present example employed the use of specific imaging parameters and pulse sequence, the present invention is not limited to these specific parameters or sequence. Any or all of the imaging parameters or pulse sequence can be altered according to sound clinical principles know in the art in order to maximize the scan.

One of the most obvious changes in going from the recumbent to the upright posture is the lung volume. It has been shown that the lung area measured on sagittal slices correlated very well with spirometry lung volume measurement. Hence, we measured the area of the lung in the mid-sagittal slice of the right lung and regarded this proxy measure of the total lung volume as the RV.

To quantify the overall signal-to-noise ratio (SNR) in the lungs in different postures, 4 regions of interest (ROI) were drawn in the peripheral lung parenchyma in a mid-sagittal slice of the right lung as illustrated in FIG. 1. The right lung was chosen instead of the left to avoid the crowding of the lung parenchyma from the heart and its main vessels. Care was taken not to include any visible blood vessels in the drawing of ROIs. The anterior ROI (A-ROI) and posterior ROI (P-ROI) were located respectively at the anterior and posterior area of the lung halfway in the S/I direction. The superior ROI (S-ROI) and inferior ROI (I-ROI) were located around the apex and bottom of the lung halfway in the A/P direction. The SNR in each ROI was calculated by dividing the average signal intensity in the ROI by the standard deviation of signal intensity in a region of air outside the body (the square in FIG. 1). Mean SNR of the lungs was then calculated by averaging the SNR of the 4 ROIs.

Mean SNR=[SNR(A-ROI)+SNR(P-ROI)+SNR(S-ROI)+SNR(I-ROI)]/4

It was previously reported that lung parenchyma MR signal intensity increased towards the posterior regions of the lungs in the supine posture and reversed direction in the prone posture. This gradation of lung parenchyma MR signal intensity in the A/P direction can be quantified to a good extent in the first order approximation as a linear variation. Hence, the A/P SNR Gradation is defined as the division of the difference between A-ROI and P-ROI SNR by the distance separating the 2 ROIs (A/P Distance in cm), and then normalized by the mean SNR of A-ROI and P-ROI to facilitate comparison with published numbers of other research groups.

A/P SNR Gradation (%/cm)=[SNR(A-ROI)−SNR(P-ROI)]*100%/[A/P Distance*{SNR(A-ROI)+SNR(P-ROI)}/2]

The signal gradation in the S/I direction was similarly defined.

S/I SNR Gradation (%/cm)=[SNR(S-ROI)SNR(I-ROI)]*100%/[S/I Distance*{SNR(S-ROI)+SNR(I-ROI))}/2]

A/P SNR Gradation and S/I SNR Gradation can take on positive or negative values. For example, a positive A/P SNR Gradation means the A-ROI has a larger SNR than the P-ROI and so on.

To determine whether the above 4 parameters (RV, Mean SNR, A/P SNR Gradation, and S/I SNR Gradation) were statistically different in the 3 postures, two-tailed Student's t-test was performed with P<0.05 considered to constitute a statistically significant difference.

Figure 2:
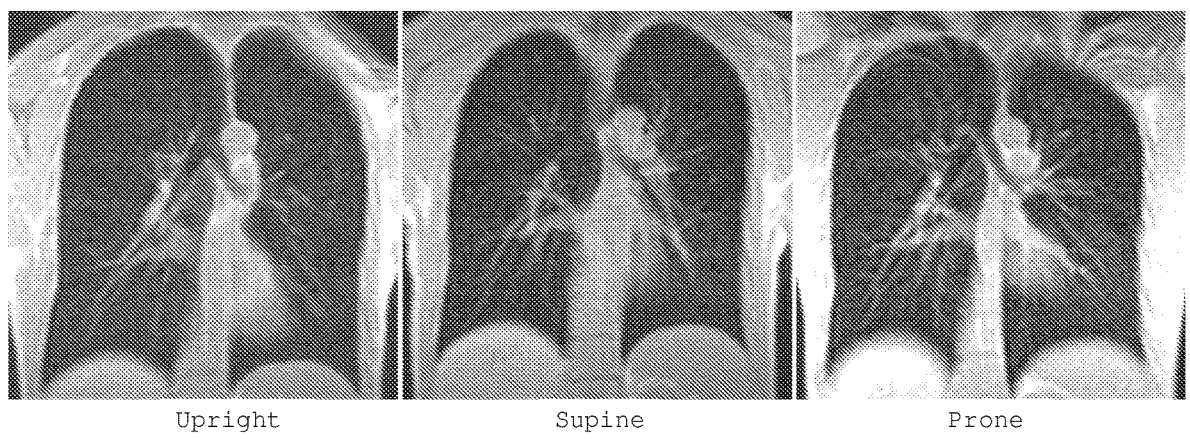
FIG. 2. depicts coronal MR images of comparable anatomical location among 3 postures for the first participant in the study discussed in the examples.

Good image quality was obtained as exemplified by the coronal images shown in FIG. 2. Blood vasculature in the chest was well visualized down to high order blood vessels. Signal from lung parenchyma was visible and above noise.

Average residual lung volume of the volunteers at end expiration increased by about 21% on going from the supine to the upright posture, and prone RV was about 5% larger than that of supine posture but the differences did not reach statistical significance.

Figure 3:
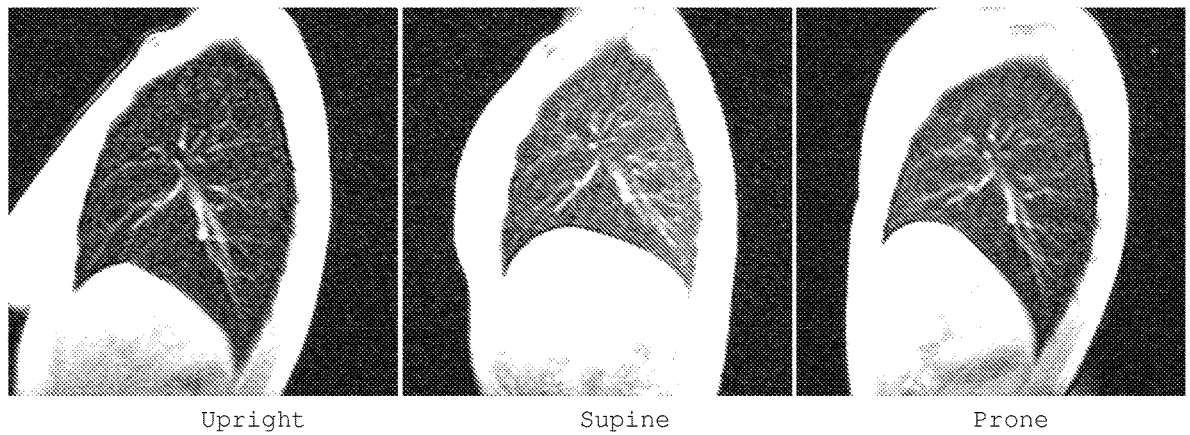
FIG. 3. depicts mid-sagittal images (windowed with the same setting) of the right lung in the 3 postures for the second participant in the study discussed in the examples.
Figure 4:
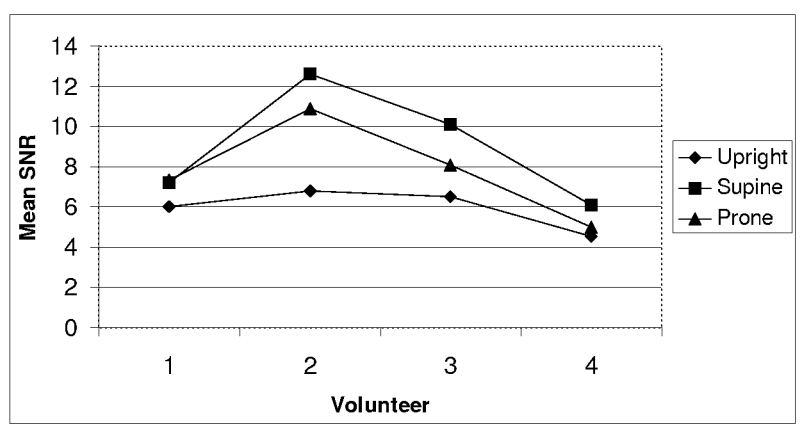
FIG. 4. depicts variation of Mean SNR of lung parenchyma MR signal intensity with postures.

A most striking difference between upright and recumbent ¹H MR lung imaging was that the lung parenchyma MR signal intensity was greatly reduced on going from the recumbent to the upright posture, as is self-evident in FIG. 3. The Mean SNR across the 4 volunteers in the 3 postures were plotted in FIG. 4. The lung parenchyma MR signal intensity was highest in the supine posture (Mean SNR=9), closely followed by the prone posture (Mean SNR=8), and lowest in the upright posture (Mean SNR=6). However, they did not reach statistically significant difference. The overall drop in Mean SNR was about 34% on going from the supine to the upright posture. As the lung volume increase was about 21% on going from the supine to the upright posture, it makes it unlikely that the variation of lung parenchyma MR signal intensity is due to lung volume change alone.

Figure 5:
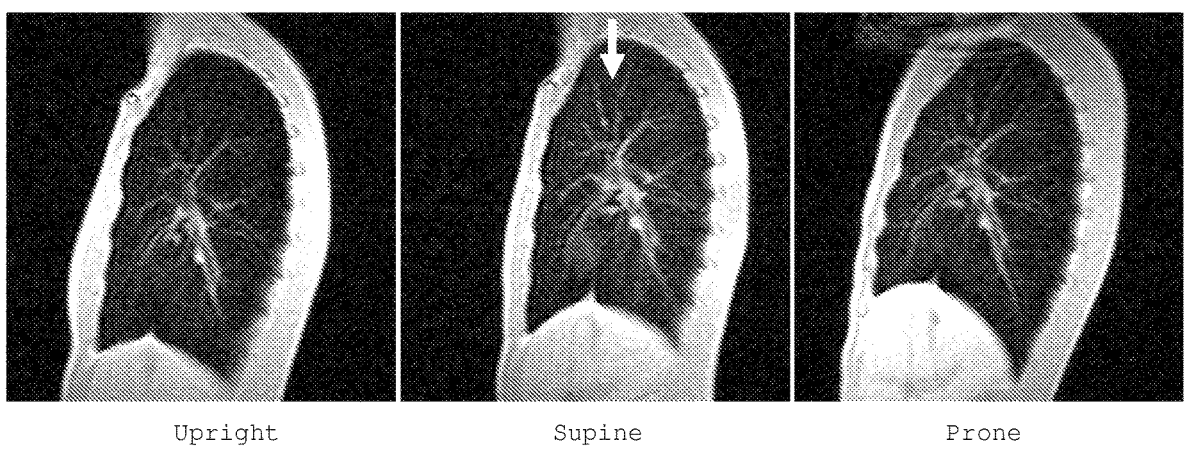
FIG. 5. depicts a white arrow indicating a region with some superiorly located blood vessels clearly visible in the supine posture and somewhat visible in the prone posture but are absent in the upright image.

Another visually recognizable finding was the reduction of blood vessel conspicuity on going from the recumbent to the upright posture. FIG. 5 was an illustration of this effect in one of the volunteers. This appeared to be a general trend among all the volunteers.

Figure 6:
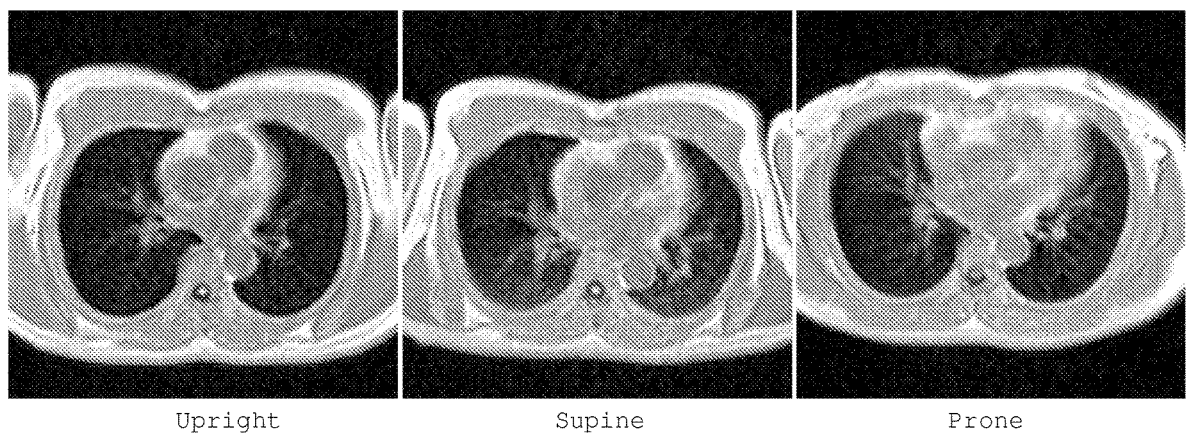
FIG. 6. depicts axial images of the third participant in the study described in the examples section in 3 postures.
Figure 7:
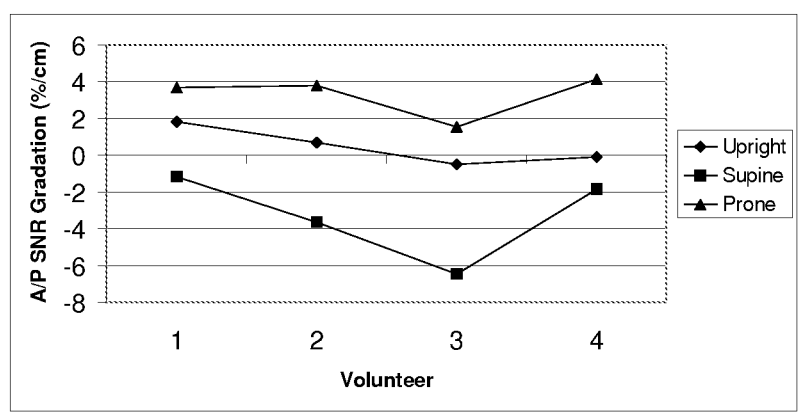
FIG. 7. depicts variation of lung parenchyma MR signal intensity along the anterior/posterior ("A/P") direction with postures.

The phenomenon of higher lung parenchyma MR signal intensity in the gravitationally dependent regions of the lungs in the supine and the prone posture was also evident. When the lungs were imaged in the upright posture in this study, this A/P signal intensity gradation was, much reduced and was not as visually apparent (FIG. 6). The quantitative plot of FIG. 7 showed that the A/P SNR Gradation in the upright posture was much less compared to that of the supine or prone posture and took on positive as well as negative values in different volunteers. On the other hand, the supine A/P SNR Gradation was always negative, indicating consistent increase of lung parenchyma MR signal intensity towards the posterior lung. Similarly, the prone A/P SNR Gradation showed consistent increase of lung parenchyma MR signal intensity towards the dependent region of the lungs anteriorly. Average A/P SNR Gradation across all 4 volunteers was 0.5%/cm for upright, −3.3%/cm for supine, and 3.3%/cm for prone posture. These were all significantly different from each other.

Figure 8:
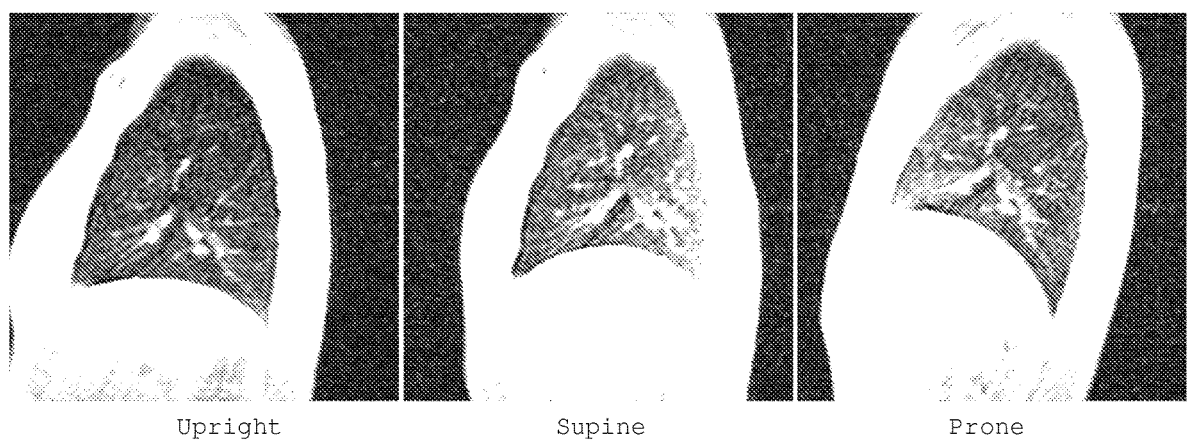
FIG. 8. depicts the increasing lung parenchyma MR signal intensity towards the inferior parts of the lungs when upright in the third study participant.
Figure 9:
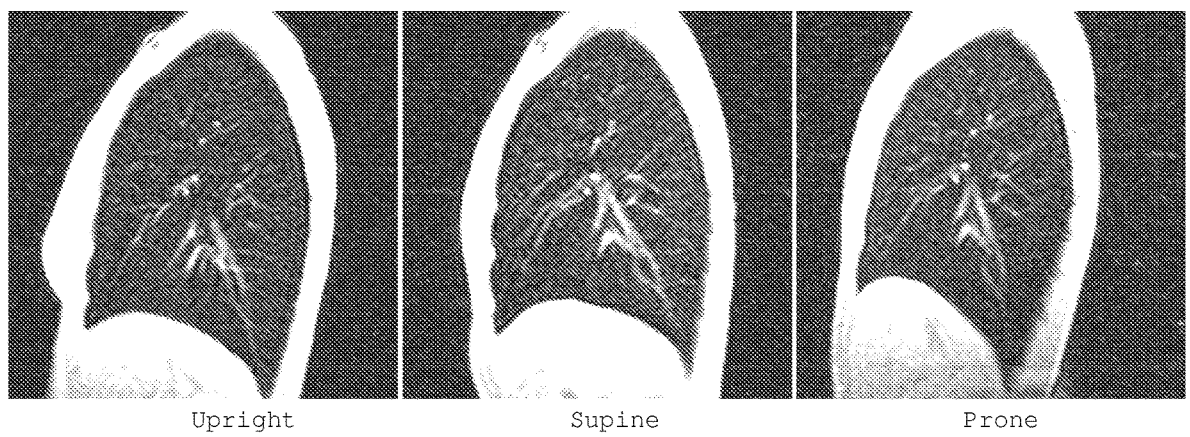
FIG. 9. depicts an example of no significant variation of lung parenchyma MR signal intensity in the superior/inferior ("S/I") direction when upright in the fourth study participant.

With regards to the spatial gradation of signal intensity along the S/I direction from the recumbent to the upright posture, greater subject variability appeared in the S/I direction than the A/P direction. For example, FIG. 8 showed a volunteer with a clear increase of lung parenchyma MR signal intensity towards the inferior portions of the lungs in the upright posture while no such trend was apparent in the volunteer of FIG. 9. Overall, 2 volunteers showed a S/I gradation of signal intensity while it was not significant in the other 2 volunteers. This was reflected in the quantitative plot of the S/I SNR Gradation in FIG. 10. On average for all volunteers, the S/I SNR Gradation was −1.9%/cm for upright, −1.1%/cm for supine, and −1.7%/cm for prone and did not reach statistically significant difference among them. The negative value of S/I SNR Gradation in all 3 postures indicated that the lung parenchyma MR signal intensity tended to increase towards the inferior lungs in all 3 postures, especially when upright and prone.

With 4 volunteers, 3 postures, and 4 ROIs in a mid-sagittal slice of the right lung, there are a total of 48 ROIs. The lung parenchyma MR SNR among these 48 ROIs spanned a large range, from 3.7 to 16.1. This underscores the highly sensitive nature of lung parenchyma MR signal intensity to postures and also to variability among individuals.

It is known in the art that gravitationally dependent regions exhibit a higher peak signal enhancement and also a faster time-to-peak than the non-dependent regions. The study indicates: −3.3%/cm for the supine positions and 3.3%/cm for prone positions.

In the upright posture, there is little spatial gradation of lung parenchyma MR signal intensity along the iso-gravitational A/P direction (A/P SNR Gradation=0.5%/cm versus 3.3%/cm for the recumbent postures). However, in the recumbent postures, a large gradation of lung parenchyma MR signal intensity in the iso-gravitational S/I direction was observed in two of the volunteers as one case was illustrated in FIG. 8. On closer examination of the images, this result is actually a manifestation of the more complex 2D nature of spatial distribution of lung parenchyma MR signal intensity. For example, the lung parenchyma MR signal intensity of volunteer 3 in FIG. 8 showed a diagonal pattern of strong signal emanating from the posterior-inferior part of the lung when supine and switched to the anterior-inferior part when prone. In volunteer 4 (FIG. 9), the diagonal pattern was also evident, though in the opposite and a weaker fashion: a low signal region emanating from the anterior-inferior part of the lung when supine and switched to the posterior-inferior part when prone. This diagonal distribution of lung parenchyma MR signal intensity resulted in a large negative S/I SNR Gradation in the recumbent postures in volunteer 1 and 3 and a small positive S/I SNR Gradation in the recumbent postures in volunteer 2 and 4.

Based on the heart's anatomical orientation within the mediastinum, the spatial variation of lung parenchyma MR signal intensity is not just confined to one orthogonal axis but also exhibits a diagonal component. On the other hand, no such diagonal trend was apparent in the upright posture in any of the volunteers. One explanation for the presence of diagonal spatial variation of lung parenchyma MR signal intensity in the recumbent postures, and its absence in the upright posture, could be that this asymmetry is being diminished by the large reduction of lung blood volume in the upright posture.

Figure 10:
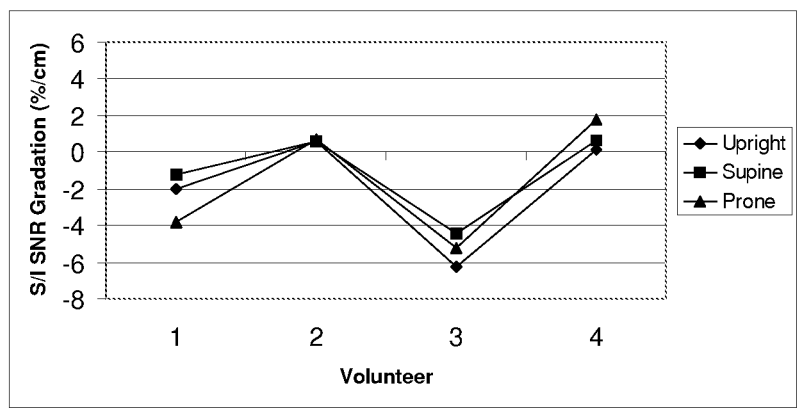
FIG. 10. depicts variation of lung parenchyma MR signal intensity along the S/I direction with postures.

Another notable observation from FIG. 10 is that S/I SNR Gradation appears to be similar across all postures within an individual. In other words, the S/I SNR Gradation seems to cluster around the same value and polarity regardless of the posture for any given individual. This makes S/I SNR Gradation more subject-dependent rather than posture-dependent, contrary to the behavior of A/P SNR Gradation.

Figure 11:
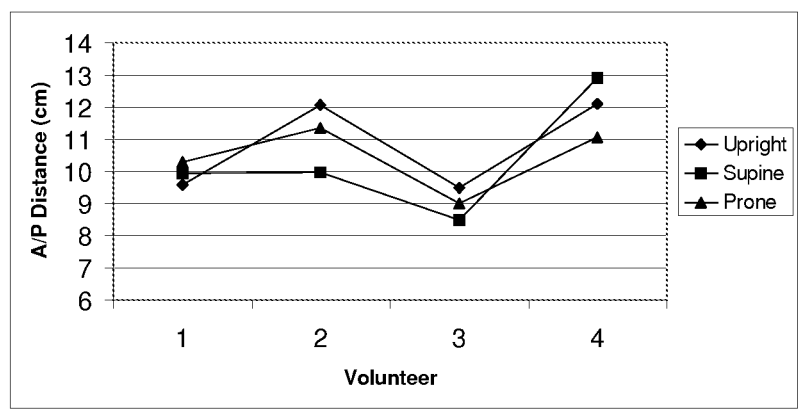
FIG. 11. depicts variation of the A/P Distance between the A-ROI and the P-ROI with postures among the volunteers.
Figure 12:
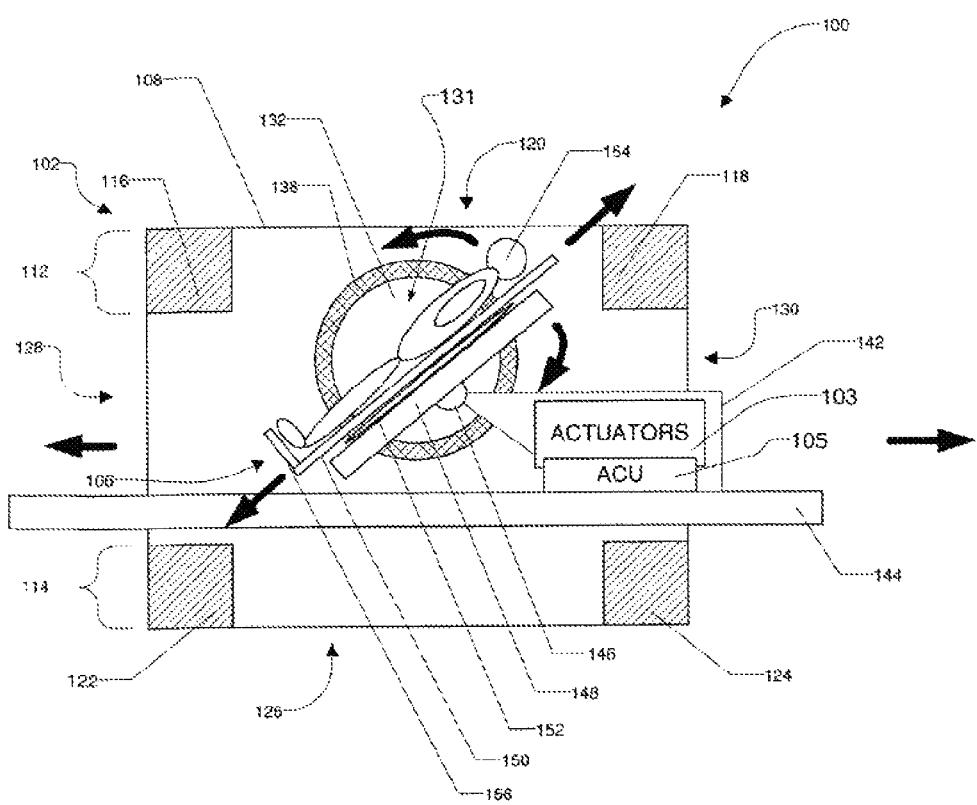
FIG. 12 depicts an example of an upright MRI device.

A major distinguishing feature between the A/P and S/I direction is that the lungs are longer in the S/I direction than in the A/P direction. For example, in the volunteer population of this study, the S/I Distance was on average larger than the A/P Distance by 38.2% when upright, 26.8% when supine, and 21.2% when prone. In order to search for what the S/I SNR Gradation could be dependent on if not heavily on posture, a correlation analysis was conducted of the S/I SNR Gradation with the 3 morphometric measures of A/P Distance, S/I Distance, and RV. We found a significant correlation of the S/I SNR Gradation with the A/P Distance (correlation coefficient=0.96, significance level=0.037) when averaged across postures but not with the other 2 measures (S/I Distance and RV). Qualitative inspection of the A/P Distance plot (FIG. 11) also corroborated its similarity with the S/I SNR Gradation profile. This rib cage size measure along the A/P direction has a similar profile to that of the S/I SNR Gradation of FIG. 10. Pearson's statistical test revealed a significant correlation between the A/P Distance and the S/I SNR Gradation when averaged across postures. Correlation analysis of the A/P SNR Gradation with the 3 morphometric measures was also performed and yielded no significant correlation relationship.

Comparison with the supine and prone posture revealed major postural changes on going from the recumbent to the upright posture: large reduction of lung parenchyma MR signal intensity, reduction of blood vessel conspicuity, and changes in the spatial distribution of lung parenchyma MR signal intensity. Due to the intimate relationship of cardiac and pulmonary functions, it is foreseeable that upright MRI may provide a new means of quantifying the efficiency of cardiac function and the extent of cardiac failure.

ALTERNATIVE EMBODIMENTS

As an alternative to the upright position, images could be captured on patients in the Trendelenburg position to see if the S/I SNR Gradation would switch to a preponderance of positive values. Further imaging of the pulmonary blood flow between the lungs and the atria could be useful to evaluate and diagnose cardiac functions. For example, it may help to determine if the subject-dependency of S/I SNR Gradation is due to cardiac function variation among volunteers.

The UPRIGHT® MRI scanner has all-posture capability, including the important upright posture. As a result, the UPRIGHT® MRI scanner is an ideal solution for proton and hyperpolarized gas MR lung imaging with multi-posture capability.

The present invention is not limited only to the use of MR signal intensity to perform the methods described herein. In other another aspects of the present invention, any type of MR signal characteristic (e.g. signal phase, signal frequency and signal amplitude) can be used either by itself or in combination, to aid the clinician in making clinical determinations about vasculature, parenchyma and or cardiac function.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for evaluating magnetic resonance signals, comprising the steps of:
    positioning the patient in a recumbent position in the magnetic resonance imaging apparatus;
    obtaining magnetic resonance signals of at least one of the patient's vasculature and parenchyma of one or more organs;
    positioning the patient in an upright position in the magnetic resonance imaging apparatus
    obtaining magnetic resonance signals of at least one of the patient's vasculature and parenchyma of the one or more organs;
    generating a first image signal corresponding to the magnetic resonance signals captured in the recumbent position and a second image signal corresponding to the magnetic resonance signals captured in the upright position;
    comparing an intensity of the first image signal with an intensity of the second image signal to evaluate gravitational effects on the one or more organs and to generate a comparison result of the intensity of the first image signal relative to the intensity of the second image signal; and
    indicating the presence of congestive heart failure based on the comparison result.

2. The method of claim 1, comprising determining the presence of fluid in the organ or organs where the comparison result indicates an intensity of the second image signal is less than an intensity of the first image signal.

3. The method of claim 1, wherein the magnetic resonance signals are used to create an image.

* * * * *